US008445877B2

(12) United States Patent
Someya et al.

(10) Patent No.: US 8,445,877 B2
(45) Date of Patent: May 21, 2013

(54) EXTREME ULTRAVIOLET LIGHT SOURCE APPARATUS AND TARGET SUPPLY DEVICE

(75) Inventors: Hiroshi Someya, Hiratsuka (JP); Tamotsu Abe, Hiratsuka (JP); Hideo Hoshino, Hiratsuka (JP)

(73) Assignee: Gigaphoton Inc., Tochigi (JP)

( * ) Notice: Subject to any disclaimer, the term of this patent is extended or adjusted under 35 U.S.C. 154(b) by 0 days.

(21) Appl. No.: 13/081,148

(22) Filed: Apr. 6, 2011

(65) Prior Publication Data

US 2011/0174996 A1 Jul. 21, 2011

Related U.S. Application Data

(63) Continuation of application No. 12/385,955, filed on Apr. 24, 2009, now Pat. No. 8,003,962.

(30) Foreign Application Priority Data

Oct. 19, 2006 (JP) ................................ 2006-285105

(51) Int. Cl.
*A61N 5/06* (2006.01)
*G01J 3/10* (2006.01)
*H05G 2/00* (2006.01)

(52) U.S. Cl.
USPC .................. 250/504 R; 250/423 R; 250/424; 250/425

(58) Field of Classification Search
USPC .......................... 250/504 R, 423 R, 424, 425
See application file for complete search history.

(56) References Cited

U.S. PATENT DOCUMENTS

| | | | | |
|---|---|---|---|---|
| 2002/0070353 A1 * | 6/2002 | Richardson | ................ | 250/492.1 |
| 2004/0108473 A1 * | 6/2004 | Melnychuk et al. | ...... | 250/504 R |
| 2006/0043319 A1 * | 3/2006 | Gaebel et al. | ............ | 250/504 R |
| 2007/0170377 A1 * | 7/2007 | Nakano | ..................... | 250/504 R |
| 2010/0019173 A1 * | 1/2010 | Someya et al. | ............ | 250/496.1 |

FOREIGN PATENT DOCUMENTS

| | | |
|---|---|---|
| JP | 2002-237448 | 8/2002 |
| JP | 2003-43199 | 2/2003 |

* cited by examiner

*Primary Examiner* — Jack Berman
*Assistant Examiner* — Meenakshi Sahu
(74) *Attorney, Agent, or Firm* — McDermott Will & Emery LLP

(57) ABSTRACT

A nozzle protection device capable of protecting a target nozzle from heat of plasma without disturbing formation of a stable flow of a target material in an LPP type EUV light source apparatus. This nozzle protection device includes a cooling unit which is formed with an opening for passing the target material therethrough, and which is formed with a flow path for circulating a cooling medium inside, and an actuator which changes a position or a shape of the cooling unit between a first state of evacuating the cooling unit from a trajectory of the target material and a second state of blocking heat radiation from the plasma to the nozzle by the cooling unit while securing a path of the target material in the cooling unit.

22 Claims, 17 Drawing Sheets

EXTREME ULTRAVIOLET LIGHT SOURCE APPARATUS AND TARGET SUPPLY DEVICE

RELATED APPLICATIONS

This application is a Continuation of U.S. patent application Ser. No. 12/385,955, filed on Apr. 24, 2009 now U.S. Pat. No. 8,003,962, claiming priority of Japanese Patent Application No. 2006-285105, filed on Oct. 19, 2006, the entire contents of each of which are hereby incorporated by reference.

BACKGROUND OF THE INVENTION

1. Field of the Invention

The present invention relates to a nozzle protection device to be used for protecting a nozzle, which injects a target material, from plasma in a laser produced plasma type extreme ultraviolet (EUV) light source apparatus, and an EUV light source apparatus provided with such a nozzle protection device.

2. Description of a Related Art

Recent years, as semiconductor processes become finer, photolithography has been making rapid progress to finer fabrication. In the next generation, microfabrication of 100 nm to 70 nm, further, microfabrication of 50 nm or less will be required. Accordingly, in order to fulfill the requirement for microfabrication of 50 nm or less, for example, exposure equipment is expected to be developed by combining an EUV light source generating EUV light having a wavelength of about 13 nm and reduced projection reflective optics.

As the EUV light source, there are three kinds of light sources, which include an LPP (laser produced plasma) light source using plasma generated by applying a laser beam to a target (hereinafter, also referred to as "LPP type EUV light source apparatus"), a DPP (discharge produced plasma) light source using plasma generated by discharge, and an SR (synchrotron radiation) light source using orbital radiation. Among them, the LPP light source has advantages that extremely high intensity close to black body radiation can be obtained because plasma density can be considerably made larger, that the light emission of only the necessary waveband can be performed by selecting the target material, and that an extremely large collection solid angle of 2π steradian can be ensured because it is a point light source having substantially isotropic angle distribution and there is no structure surrounding the light source such as electrodes. Therefore, the LPP light source is considered to be predominant as a light source for EUV lithography, which requires power of more than several tens of watts.

Here, a principle of generating EUV light in the LPP type EUV light source apparatus will be briefly explained. By injecting a target material from a nozzle and applying a laser beam to the target material, the target material is excited and turned into plasma. Various wavelength components including extreme ultraviolet (EUV) light are radiated from thus generated plasma. Then, the EUV light is reflected and collected by using a collector mirror, which selectively reflects a desired wavelength component (e.g., a component having a wavelength of 13.5 nm) of them, and outputted to an exposure unit. For example, as the collect mirror collecting the EUV light having a wavelength near 13.5 nm, a mirror having thin films of molybdenum (Mo) and silicon (Si) which are alternately stacked on a reflecting surface is used.

The state of the target material to be supplied into the chamber has been studied variously. For the supply of the target material in a liquid state, there is a case of forming a continuous flow (target jet or continuous jet) of the target material or a case of forming a droplet-like target (droplet target). In the latter case, the droplet target is formed by a method of stirring the target material by providing vibration at a predetermined frequency to the target jet by using a vibration mechanism.

Meanwhile, in such an EUV light source apparatus, there is a problem that the nozzle for supplying the target material (target nozzle) is damaged considerably and has a short life. Although it is preferable to dispose the target nozzle in the neighborhood of an application position of the laser beam, that is, a plasma emission point in order to apply the laser beam accurately on the target material, the target nozzle is exposed to high temperature heat generated from the plasma and the temperature of the target nozzle increases extraordinarily. Further, flying particles (debris) such as fast ions or neutral particles, which are emitted from the plasma, shave components such as the target nozzle, a vibrator element, and so on by collision, and the debris attach to these components. Thereby the performances of the components are considerably deteriorated.

As a related technology, US Patent Application Publication US 2006/0043319 A1 discloses a target supply unit for the energy beam-induced generation of short-wavelength electromagnetic radiation in which a nozzle protection device is provided in the interaction chamber between the target nozzle and the plasma generation point (light emission point) (see page 1). This nozzle protection device includes a gas pressure chamber having an opening formed along a target trajectory so as not to prevent a target flow, and the gas pressure chamber is filled with buffer gas which is maintained to have a pressure of approximately several tens of millibars (see FIG. 1). This nozzle protection device prevents flying particles from the plasma from reaching the nozzle (sputter shield) by the gas filling a space through which the target material passes. Further, FIG. 3 in US 2006/0043319 A1 shows a short-wavelength electromagnetic radiation generating apparatus further provided with a heat protection plate in addition to such a sputter shield. This heat protection plate blocks heat generated from the plasma by circulation of cooling medium (heat shield).

Meanwhile, in the case of forming the target jet or the droplet target, a certain time is required until the target material injected from the target nozzle gets to have a predetermined injection pressure. Further, in this pressure increasing process (initial stage of target formation), the target material becomes spray like state, or injected intermittently, or injected from the nozzle in a direction different from a normal direction, for example, and thus, an injection state of the target material becomes unstable. In US 2006/0043319 A1, however, such a target formation initial stage is not taken into consideration, and there is a problem that the opening for passing the target material is blocked when the target material in the unstable state is sprayed onto the sputter shield or the heat protection plate.

From a viewpoint of protecting the target nozzle from the plasma heat, it is preferable to make the opening diameter of the heat protection plate as small as possible. Further, the target material flow including target jet or the droplet target becomes more unstable in the lower downstream. Accordingly, it is preferable to dispose the heat protection plate close to the injection outlet of the target nozzle. However, when the opening diameter of the heat protection plate is made smaller and further the heat protection plate is disposed close to the nozzle injection outlet, there arises a problem that the target material is attached and deposited onto the neighborhood of the opening at the target formation initial stage. As a result, a flow of the target material becomes disturbed, or the opening of the heat protection plate becomes blocked. On the other hand, when the opening diameter of the heat protection plate is increased for avoiding the above problem, the shield effect against the plasma heat becomes reduced. Alternatively, when the heat protection plate is disposed apart from the target nozzle, the position of the target material becomes unstable and accordingly the opening diameter has to be made larger. Also in this case, the heat shield effect will be reduced. In US 2006/0043319 A1, such instability of the target material position and a dilemma resulting therefrom are also not taken into consideration.

Japanese Patent Application Publication JP-P2002-237448A discloses an extreme ultraviolet light lithography apparatus utilizing a thin film protection coating for protecting a plurality of hardware elements disposed near a laser produced light source, from an erosion effect of energy particles which are emitted from the laser produced light source, in order to reduce an erosion effect of ion sputtering. That is, JP-P2002-237448A prevents a collector mirror from being contaminated by a sputtered material, which is generated by sputtering of a hardware surface with ions or neutral particles emitted from plasma (fire ball), by covering hardware such as a target nozzle and a target collecting tube with a diamond thin film, for example. In particular, the target nozzle is provided with an under coat of nickel (Ni) on a main body made of copper, and further a diamond thin film formed thereon, thereby increasing its strength.

Further, Japanese Patent Application Publication JP-P2003-43199A discloses a nozzle including (i) a main body having a source end portion for receiving a target material, an output end portion for injecting a spray of the target material, and a channel therebetween, and (ii) a target material transfer tube extending through the channel. This target material transfer tube includes a first end disposed close to the source end portion of the nozzle and a second end portion disposed close to the output end portion of the nozzle and having an expandable opening, in which the first end portion receives the target material and the second end portion injects the target material to the output end portion of the nozzle through the expandable opening. That is, in JP-P2003-43199A, the target material transfer tube is thermally insulated from the outside by use of a protection cap (apart of the main body) for preventing intensity reduction, which is caused by heat up of the nozzle, in the target material injected from the nozzle. In JP-P2003-43199A, the protection cap is formed of graphite, and the transfer tube is formed of stainless steel.

In JP-P2002-237448A and JP-P2003-43199A, the surface of the nozzle or the like is formed with diamond or graphite for suppressing the sputtering phenomenon caused by the flying particles from the plasma. A diamond thin film, for example, has a high thermal conductivity and an anti-sputtering property, and is surely difficult to be sputtered. However, the sputtering phenomenon cannot be perfectly prevented, and therefore, even in a small amount, sputtered particles of carbon are also generated. When such sputtered particles reach a collector mirror and are deposited on the reflection surface thereof, this reduces the reflectivity of the collector mirror. As a result, life is reduced in the collector mirror which is far more expensive than the target nozzle.

As described above, in the conventional heat shield, the instability at the target formation initial stage is not taken into consideration, and the material of the heat shield is selected only in view of extension of the nozzle life. According to the conventional technology, although the original object of the heat shield for protecting the nozzle from the flying particles such as ions emitted from the plasma and from the heat generated from the plasma could be achieved, a flow of the target material could not be realized stably, and a long-term influence (e.g., life shortening) to the peripheral components including the collector mirror could not be avoided. That is, in view of industrial application, there has been a problem that the EUV light source apparatus has a low reliability and a high running cost.

SUMMARY OF THE INVENTION

The present invention has been achieved in view of such a problem. An object of the present invention is to provide a nozzle protection device capable of protecting a target nozzle from heat of plasma without disturbing formation of a stable flow of a target material in an LPP type EUV light source apparatus.

In order to achieve the above object, a nozzle protection device according to one aspect of the present invention is a nozzle protection device to be used in an extreme ultraviolet light source apparatus for generating extreme ultraviolet light by applying a laser beam to a target material injected from a nozzle and thereby turning the target material into plasma, and the nozzle protection device comprises: a cooling unit which is formed with an opening for passing the target material therethrough, and which is formed with a flow path for circulating a cooling medium inside; and an actuator which changes at least one of a position and a shape of the cooling unit between a first state of evacuating the cooling unit from a trajectory of the target material and a second state of blocking heat radiation from the plasma to the nozzle by the cooling unit while securing a path of the target material in the cooling unit.

According to the one aspect of the present invention, the cooling unit is provided which is formed with the opening for passing the target material therethrough and the flow path for circulating the cooling medium inside, and the actuator is provided which changes the position or the shape of the cooling unit. Thereby, it is possible to realize an operation of evacuating the cooling unit from the trajectory of the target material until the target material flow is stabilized, and an operation of moving the cooling unit to a position where the target nozzle is protected from the heat of plasma after the target material flow is stabilized. Accordingly, it becomes possible to generate the EUV light stably and also to realize a long life of the target nozzle.

DESCRIPTION OF THE PREFERRED EMBODIMENTS

Hereinafter, embodiments of the present invention will be described in detail with reference to the drawings. The same constituent is denoted by the same reference symbol and explanation thereof will be omitted.

Figure 1:
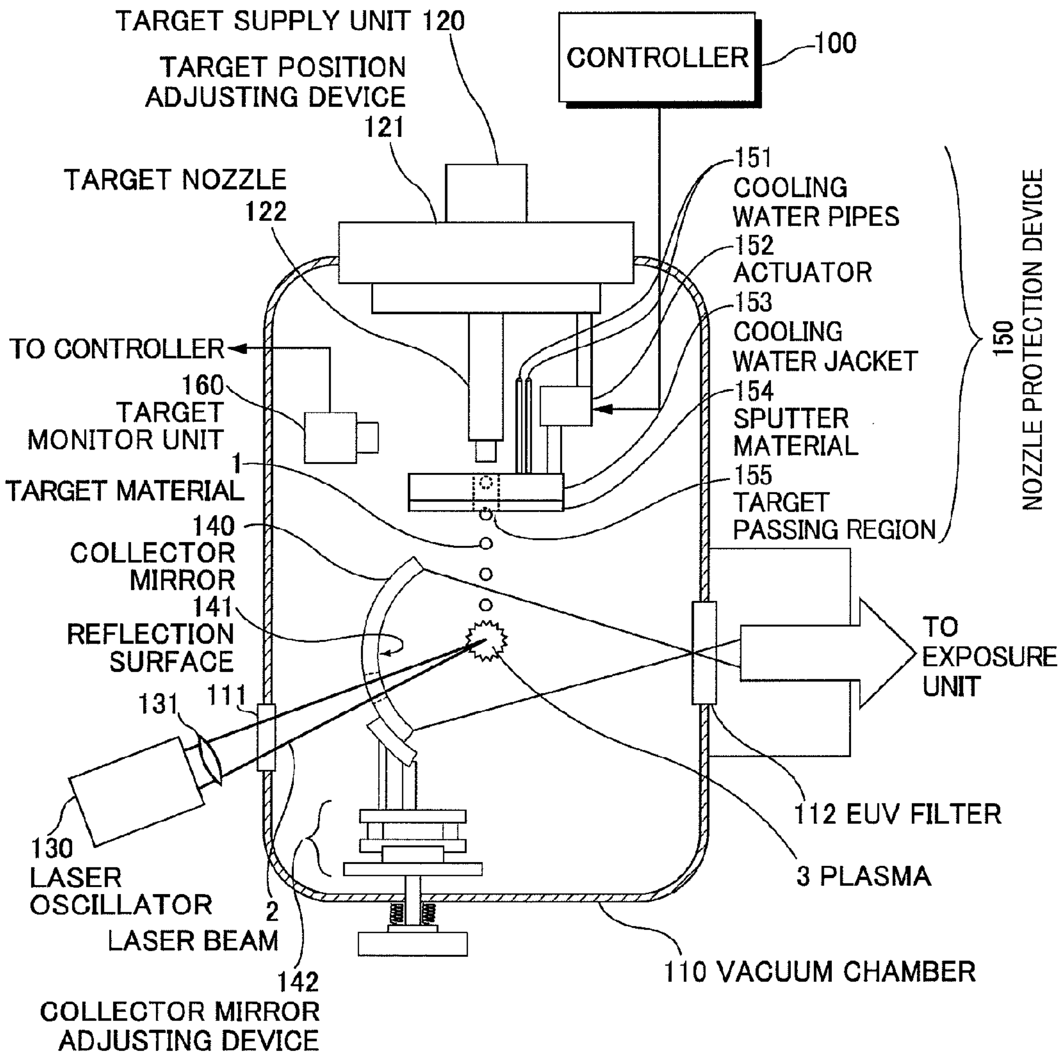
FIG. 1 is a schematic diagram showing the inside of an extreme ultraviolet light source apparatus provided with a nozzle protection device according to a first embodiment of the present invention.

FIG. 1 is a schematic diagram showing the inside of an extreme ultraviolet (EUV) light source apparatus provided with a nozzle protection device according to a first embodiment of the present invention.

As shown in FIG. 1, the EUV light source apparatus includes a controller 100, a vacuum chamber 110 in which EUV light is generated, a target supply unit 120, a target position adjusting device 121, and a laser oscillator 130. In the vacuum chamber 110, there are provided a target nozzle 122, a collector mirror 140, a nozzle protection device 150, and a target monitor unit 160.

The vacuum chamber 110 is provided with a window 111 for passing a laser beam 2, and an EUV filter 112 passing the generated EUV light. The EUV filter 112 is a filter selectively passing a predetermined wavelength component (e.g., a component having a wavelength of 13.5 nm) and prevents an unnecessary wavelength component from entering the side of exposure unit.

The target supply unit 120 supplies a target material to the target nozzle 122. The target material is a material which is excited and turned into plasma when irradiated with the laser beam 2. As the target material, xenon (Xe), a mixture containing xenon as the main component, argon (Ar), krypton (Kr), water ($H_2O$) or alcohol which becomes a gas state in a low pressure atmosphere, molten metal such as tin (Sn) or lithium (Li), water or alcohol in which small metal particles of tin, tin oxide, copper, or the like are dispersed, ionic solution dissolving lithium fluoride (LiF) or lithium chloride (LiCl) in water, or the like can be used.

The state of the target material may be any of gas, liquid, and solid at normal temperature. For example, in the case of using a material which is in a gas state at normal temperature such as xenon for the liquid target, the target supply unit 120 liquefies xenon gas by providing pressure and refrigeration, and supplies the liquid xenon to the target nozzle 122. On the other hand, in the case of using a material which is in a solid state at normal temperature such as tin for the liquid target, the target supply unit 120 liquefies tin by heating, and supplies the liquid tin to the target nozzle 122.

A target position adjusting device 121 adjusts the position of the target nozzle 122 such that the target material 1 is supplied accurately to a plasma emission point (a position where the laser beam 2 is applied onto the target material 1).

The target nozzle 122 injects the target material 1 supplied from the target supply unit 120, thereby forms a target jet (jet flow) or a droplet target (liquid drop), and supplies it to the plasma emission point. In the case of forming the droplet target, a vibration mechanism is further provided for vibrating the target nozzle 122 at a predetermined frequency.

The laser oscillator 130 is a laser beam source capable of pulse oscillating at a high repetition frequency, and emits the laser beam 2 for exciting the target material. Further, a focusing lens 131 is disposed on a light path of the laser beam 2 emitted from the laser oscillator 130 and thereby focuses the laser beam 2 emitted from the laser oscillator 130 onto the plasma emission point. Although the focusing lens 131 is used in FIG. 1, a focusing optics may be configured with another optical component or a combination of a plurality of optical components.

The laser beam 2 is applied to the target material 1 which is injected from the target nozzle 122, and thereby, the plasma is generated and light having various wavelengths is radiated. A predetermined wavelength component (e.g., a component having a wavelength of 13.5 nm) of the light is reflected and collected by the collector mirror 140. This EUV light is outputted through the filter 112 and output optics to the exposure unit.

The collector mirror 140 has a reflection surface 141 which selectively reflects the EUV light having a predetermined wavelength (e.g., a component having a wavelength of 13.5 nm) and focuses the EUV light onto a predetermined position. On this reflection surface 141, a Mo/Si multilayered film is formed in which molybdenum (Mo) and silicon (Si) are stacked alternately. Such a collector mirror 140 is supported by a collector mirror adjusting device 142 and is accurately aligned so as to reflect and focus the plasma radiation light generated at the plasma emission point onto a focusing point on the EUV filter 112, for example.

The collector mirror adjusting device 142 includes a plurality of stages which can be moved in three dimensions, and adjusts the position and orientation of the collector mirror 140 by driving these stages under the control of the controller 100. A supporting member of the collector mirror adjusting device 142 is mounted outside the vacuum chamber 110 and coupled to the vacuum chamber 110 via a bellows or the like. The reason of disposing the supporting member in this manner is that the stages are to be isolated from mechanical vibration and heat conduction of the vacuum chamber 110.

The nozzle protection device 150 includes cooling water pipes 151, an actuator 152, and a cooling water jacket (cooling unit) 153. Further, a sputter material 154 is disposed on the lower surface (a surface facing the plasma) of the cooling water jacket 153. Such a nozzle protection device 150 is coupled to the target position adjusting device 121 and moved together with the target nozzle 122.

The cooling water pipes 151 are provided for supplying cooling water, which is supplied from the outside of the vacuum chamber 110, to the inside of the cooling water jacket 153, and ejecting the cooling water from the cooling water jacket 153. The cooling water pipes 151 are disposed to be shadowed from the plasma 3 by the cooling water jacket 153. This is because of preventing a damage caused by the flying particles from the plasma 3. Although the cooling water jacket 153 is cooled with the water in the present embodiment, cooling medium other than the water may be used.

The actuator 152 changes the position and shape of the cooling water jacket 153 under the control of the controller 100. The operation of the actuator 152 will be described in detail hereinafter.

The cooling water jacket 153 is normally cooled by the cooling water supplied from the cooling water pipe 151 and protects the target nozzle 122 by blocking the heat generated from the plasma 3. Further, the cooling water jacket 153 is formed with an opening (target passing region) for passing the target material 1 injected from the target nozzle 122 therethrough. In the present embodiment, the diameter of the target passing region 155 is set to be 2 mm. Such a cooling water jacket 153 is disposed close to the target nozzle 122 such that the distance to the lower end of the target nozzle 122 becomes approximately 1 mm, for example. Further, the sputter material 154 is disposed on the lower surface (a surface facing the plasma) of this cooling water jacket 153. In the present embodiment, silicon (Si), which is one of the materials forming the reflection surface 141 of the collector mirror 140, is used as the sputter material 154.

The target monitor unit 160 includes an imaging device such as a. CCD, for example, and images the target material 1 injected from the target nozzle 122 to output an image signal to the controller 100. This image signal is used for controlling the operation of the nozzle protection device 150.

Figure 2A:
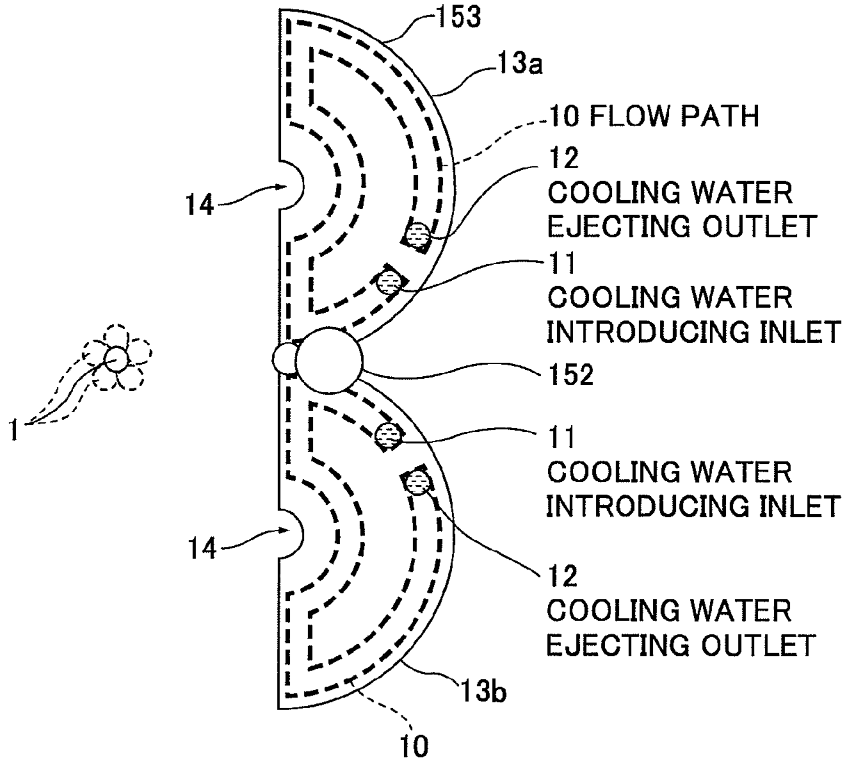
FIGS. 2A and 2B are plan views showing a cooling water jacket as shown in FIG. 1.
Figure 2B:
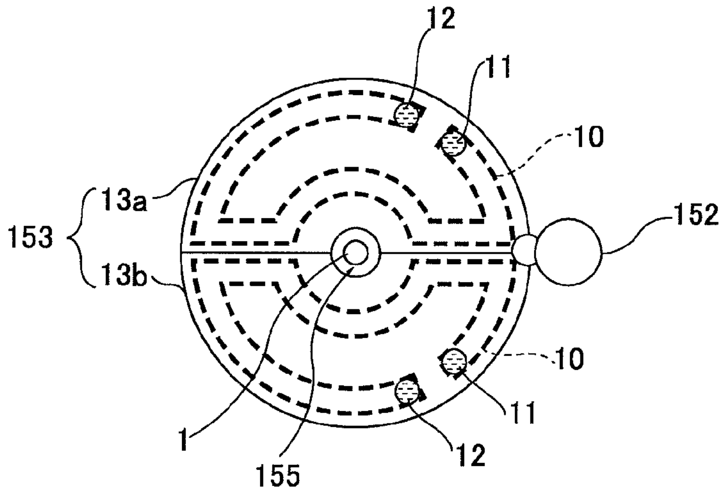

FIGS. 2A and 2B are plan views showing the cooling water jacket 153 as shown in FIG. 1. FIG. 2A shows an open state of the cooling water jacket 153, and FIG. 2B shows a closed state of the cooling water jacket 153.

As shown in FIG. 2A, the cooling water jacket 153 includes two divided parts 13*a* and 13*b* having semi circular shapes. Each of the two parts 13*a* and 13*b* is formed therein with a flow path 10 for circulating the cooling water, and this flow path 10 is provided with a cooling water introducing inlet 11 and a cooling water ejecting outlet 12. The cooling water introducing inlet 11 and the cooling water ejecting outlet 12 are connected with the cooling water pipes 151 as shown in FIG. 1. The shape of the flow path 10 and the positions of the cooling water introducing inlet 11 and the cooling water ejecting outlet 12 are not limited to those as shown in FIGS. 2A and 2B, and various shapes and dispositions may be employed therefor. Further, each of the two parts 13*a* and 13*b* is formed with a recess 14 which forms the target passing region 155 (refer to FIG. 2B) when the two parts 13*a* and 13*b* are closed.

Next, the operation of the nozzle protection device 150 as shown in FIG. 1 will be described. This nozzle protection device 150 is controlled by the controller 100 according to an observation result of the target monitor unit 160.

The controller 100 as shown in FIG. 1 provides image processing to the image signal sequentially outputted from the target monitor unit 160, and according to a result thereof, determines whether the position and the state of the target material 1 is stable or not. For example, a reference image signal is preliminarily prepared based on a binary image obtained from an image when the flow of the target material 1 is stable, and a difference between the reference image signal and the image signal outputted from the target monitor unit 160 and provided with binarization processing is calculated. Then, the controller 100 determines that the flow is unstable when a total sum of the difference values in all pixels is equal to or larger than a predetermined value, and determines that the flow is stable when the total sum of the difference values is smaller than the predetermined value.

For example, soon after the supply of the target material 1 is started, the trajectory of the target material 1 is not stabilized constantly or apart of the target material diffuses as a mist or becomes a spray state. When the flow state of the target material 1 is unstable in this manner, the actuator 152 opens the cooling water jacket 153 as shown in FIG. 2A. Thereby, the target material 1 in the unstable state does not interfere with the cooling water jacket. In this state, the laser beam 2 (FIG. 1) is not applied.

Further, when the pressure inside the target nozzle 122 increases sufficiently, the position and the state of the target material 1 become stable. Then, the actuator 152 closes the two parts 13*a* and 13*b* of the cooling water jacket 153 as shown in FIG. 2B. Thereby, the space between the target nozzle 122 and the plasma emission point is divided. Further, the target material 1 is supplied to the plasma emission point through the target passing region 155 formed thereby. The application of the laser beam 2 (FIG. 1) to the target material 1 is started after this state has been realized.

In this manner, in the present embodiment, the cooling water jacket 153 is opened and evacuated from the trajectory of the target material 1 so as not to disturb the target formation when the flow of the target material 1 is unstable. Further, after confirming that the target material 1 has been stabilized, the cooling water jacket 153 is closed and the application of the laser beam 2 is started. When the flow of the target material 1 is stable, even if the diameter of the target passing region 155 is small, it is possible for the target material 1 to pass through the target passing region 155. For example, even if the target material 1 has a diameter of approximately 20 μm, the target material 1 does not fill the target passing region 155 having a diameter of approximately 2 mm. Further, during the generation of the plasma 3, the closed cooling water jacket 153 blocks the heat from the plasma 3 and the flying particles such as ions and radicals from the plasma 3, and thereby, it becomes possible to prevent the target nozzle 122 from being damaged and to realize a long life of the target nozzle 122.

Here, there is a case that the flying particles from the plasma 3 hit the sputter material 154 disposed on the lower surface of the cooling water jacket 153 and the sputter material 154 itself is sputtered. However, the sputter material 154 is formed of silicon (Si) which is one of the materials forming the reflection surface 141 of the collector mirror 140 (FIG. 1). Therefore, even if the sputtered silicon particle is attached and deposited on the reflection surface 141 of the collector mirror 140, the reflectivity thereof is not reduced considerably. Accordingly, it becomes possible to realize a long life of the collector mirror 140.

Further, since the nozzle protection device 150 is moved together with the target nozzle 122, even when the trajectory of the target material 1 is adjusted in order to adjust the focusing point of the EUV light (e.g., a point on the EUV filter 112), it is possible to avoid the interference between the target material 1 and the nozzle protection device 150.

As described above, according to the present embodiment, cost and time required for the maintenance of the target nozzle or the collector mirror is reduced, and thereby, it becomes possible to reduce the running cost of the EUV light source apparatus. Further, since the stability of the target material flow can be maintained, it becomes possible to greatly improve the reliability of the EUV light source apparatus.

Although silicon is used for the sputter material 154 in consideration of thermal conductivity in the present embodiment, molybdenum (Mo), which is the other of the materials forming the reflection surface of the collector mirror, may be used. Further, although the sputter material 154 is attached on the lower surface of the cooling water jacket 153 in the present embodiment, a film of silicon or molybdenum may be formed on the surface of the cooling water jacket 153.

Next, a nozzle protection device according to a second embodiment of the present invention will be described.

Figure 3A:
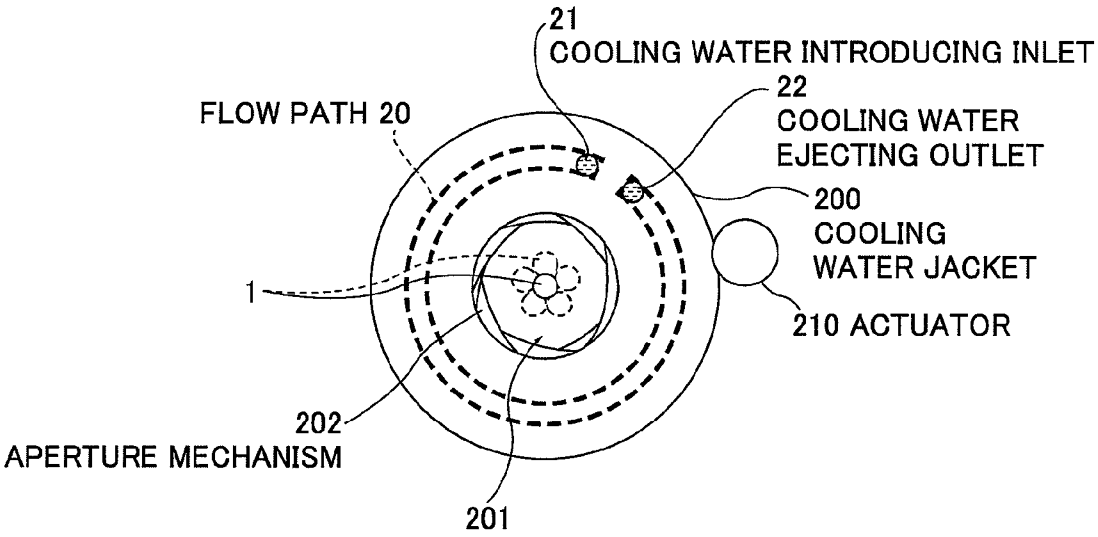
FIGS. 3A and 3B are diagrams for illustrating a nozzle protection device according to a second embodiment of the present invention.
Figure 3B:
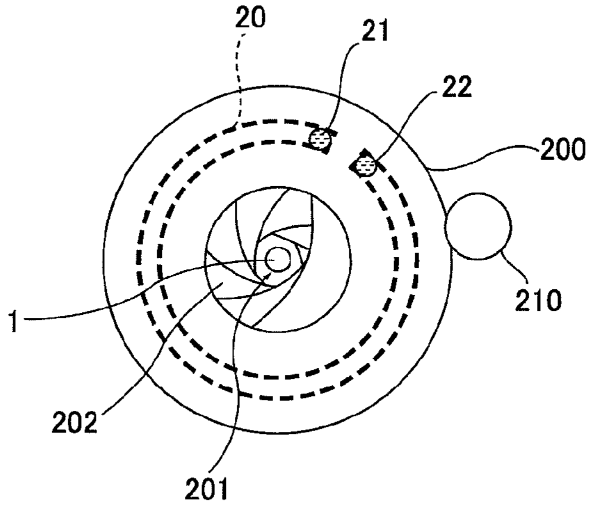

FIGS. 3A and 3B are plan views showing a part of the nozzle protection device according to the second embodiment of the present invention. As shown in FIGS. 3A and 3B, this nozzle protection device includes a cooling water jacket (cooling unit) 200, and an actuator 210 which operates under the control of the controller 100 as shown in FIG. 1. Other constituents and an arrangement of the nozzle protection device in the vacuum chamber are the same as those as shown in FIG. 1.

A target passing region 201 is formed at the center of the cooling water jacket 200, and an aperture mechanism 202 having the same structure as that of an aperture of a camera is provided on the inner perimeter of the cooling water jacket 200. The aperture mechanism 202 is driven by the actuator 210 so as to increase a diameter of the target passing region 201 as shown in FIG. 3A or reduce the diameter as shown in FIG. 3B.

Further, within the cooling water jacket 200, a flow path 20 is formed for circulating cooling water, and a cooling water introducing inlet 21 and a cooling water ejecting outlet 22 are provided at parts of the flow path 20. The cooling water introducing inlet 21 and the cooling water ejecting outlet 22 are connected with cooling water pipes 151 in the same manner as in the configuration shown in FIG. 1. Further, a sputter material such as silicon is disposed on the lower surface (a surface facing the plasma) of the cooling water jacket 200.

The actuator 210 increases the diameter of the target passing region 201 when the flow of the target material 1 is unstable so as to prevent the target material 1 from attaching to the cooling water jacket 200. Further, the actuator 210 decreases the diameter of the target passing region 201 when the flow of the target material 1 becomes stable so as to block the heat generated from plasma when the EUV light is generated.

In the present embodiment, since the diameter of the target passing region 201 can be changed as desired by the provided aperture mechanism 202, it becomes possible to use the nozzle protection device even when the diameter of the target nozzle 122 (FIG. 1) is changed. Further, even when the diameter of the target passing region 201 is changed, the outer shape of the cooling water jacket 200, that is, the size of the whole nozzle protection device is never changed, and therefore, it is possible to save the disposition space in the vacuum chamber 110.

Next, a nozzle protection device according to a third embodiment of the present invention will be described.

Figure 4A:
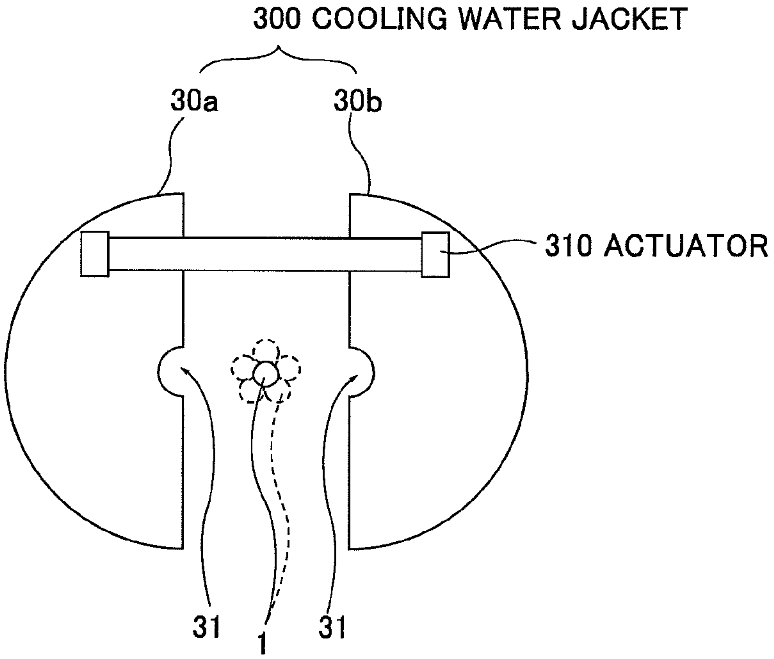
FIGS. 4A and 4B are diagrams for illustrating a nozzle protection device according to a third embodiment of the present invention.
Figure 4B:
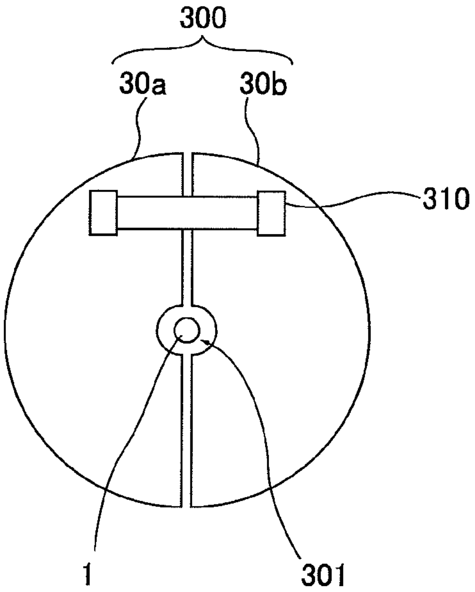

FIGS. 4A and 4B are plan views showing a part of the nozzle protection device according to the third embodiment of the present invention. As shown in FIGS. 4A and 4B, this nozzle protection device includes a cooling water jacket (cooling unit) 300 and an actuator 310 which operates under the control of the controller 100 as shown in FIG. 1. Other constituents and an arrangement of the nozzle protection device in the vacuum chamber are the same as those shown in FIG. 1.

The cooling water jacket 300 includes two divided parts 30*a* and 30*b* having semi-circular shapes. As shown in FIG. 4A, each of the parts 30*a* and 30*b* is formed with a recess 31 which forms a target passing region 301 (refer to FIG. 4B) when the two parts are closed. Further, each of the two parts 30*a* and 30*b* is formed with a flow path, and further, a cooling water introducing inlet and cooling water ejecting outlet which are connected with the cooling water pipes 151 (FIG. 1) in the same manner as in the configuration shown in FIGS. 2A and 2B. Further, a sputter material such as silicon is disposed on the lower surface (a surface facing the plasma) of the cooling water jacket 300.

The actuator 310 couples the two parts 30*a* and 30*b* having semi-circular shape with each other, and opens or closes the two parts 30*a* and 30*b* while keeping them in the horizontal direction. That is, when the flow of the target material 1 is unstable, the actuator 310 increases the gap between the two parts 30*a* and 30*b* as shown in FIG. 4A to prevent the target material 1 from attaching to the cooling water jacket 300. On the other hand, when the flow of the target material 1 becomes stable, the actuator 310 closes the two parts 30*a* and 30*b* as shown in FIG. 4B to form the target passing region 301 for passing the target material therethrough and also block the heat generated from the plasma when the EUV light is generated.

According to the present embodiment, it is possible to realize a space saving for the nozzle protection device with the simple structure.

Next, a nozzle protection device according to a fourth embodiment of the present invention will be described.

Figure 5A:
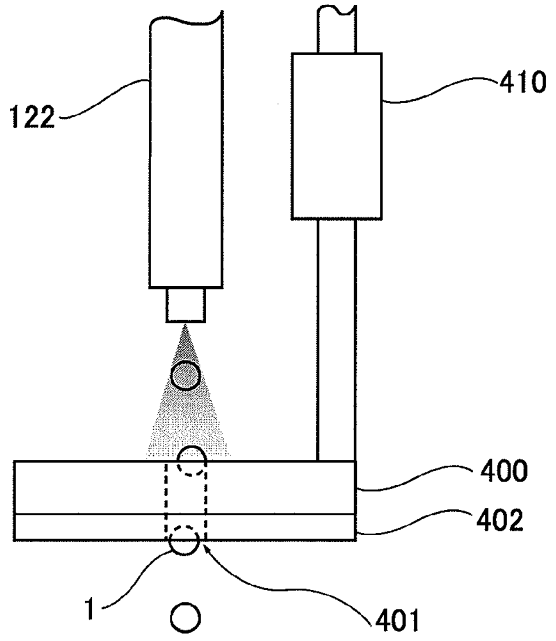
FIGS. 5A and 5B are diagrams for illustrating a nozzle protection device according to a fourth embodiment of the present invention.
Figure 5B:
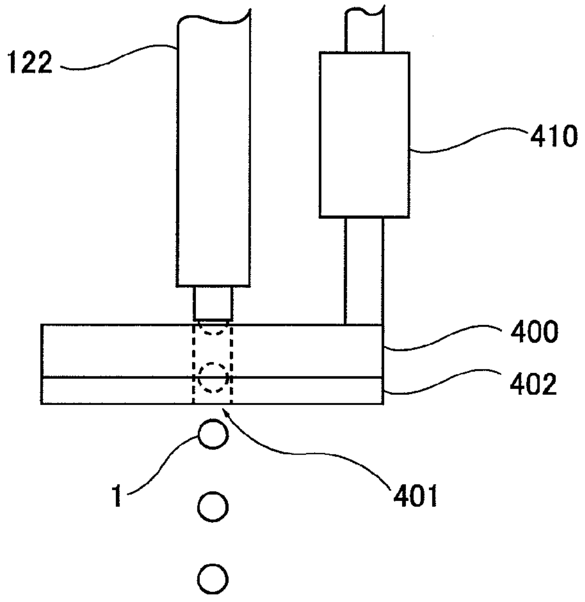

FIGS. 5A and 5B are side views showing a part of the nozzle protection device according to the fourth embodiment of the present invention. In the case of using a liquefied gas such as liquefied xenon (Xe) as the target material, even if the target material attaches to the peripheral or the inside of the target passing region in the nozzle protection device, the target material is easily evaporated within the vacuum chamber. In such a case, it is effective to use the nozzle protection device according to the present embodiment.

As shown in FIGS. 5A and 5B, the nozzle protection device according to the present embodiment includes a cooling water jacket (cooling unit) 400 and an actuator 410 which operates under the control of the controller 100 as shown in FIG. 1.

The water cooling unit 400 has a disk shape, for example, and a target passing region 401 is formed at the center thereof. Further, within the cooling water jacket 400, a flow path, and further, a cooling water introducing inlet and cooling water ejecting outlet which are connected with the cooling water pipes 151 (FIG. 1) are formed in the same manner as in the configuration shown in FIGS. 2A and 2B. Further, a sputter material 402 such as silicon is disposed on the lower surface (a surface facing the plasma) of the cooling water jacket 400.

The actuator 410 changes the distance between the lower end of the target nozzle 122 and the cooling water jacket 400 by moving the cooling water jacket 400 upward or downward.

That is, when the flow of the target material 1 is unstable, the cooling water jacket 400 is lowered to a position apart from the target nozzle 122 as shown in FIG. 5A. For example, when the target nozzle 122 has a diameter of 50 μm, the gap between an injection outlet of the nozzle 122 and the cooling water jacket 400 is set to be approximately 30 mm. As a result, the target material 1 of the liquefied gas once attaches to the inside or the peripheral of the target passing region 401 but is evaporated rapidly.

Here, since the target nozzle 122 is cooled by injecting the liquefied gas, if ice of the liquefied gas is attached to the nozzle side (neighborhood of the injection outlet), it cannot be removed easily. In this case, even when the pressure inside the nozzle reaches a sufficient value (e.g., 1 MPa), the stable flow of the target material 1 cannot be formed due to the ice deposited near the nozzle injection outlet. Accordingly, in the present embodiment, the cooling water jacket 400 is evacuated to a position sufficiently apart from the target nozzle 122 such that the ice deposited in the neighborhood of the target passing region 401 does not attach to the target nozzle 122.

On the other hand, when the flow of the target material 1 becomes stable, the cooling water jacket 400 is lifted upward and disposed close to the target nozzle 122 (e.g., at a position lower than the injection outlet of the nozzle 122 by approximately 1 mm) as shown in FIG. 5B. This improves accuracy of the position relationship when the target material 1 passes through the target passing region 401. For example, even when the target material 1 has a diameter of approximately 50 μm, it can easily pass through the target passing region 401 having a diameter of approximately 3 mm. Further, at the same time, the heat and the flying particles generated from the plasma are blocked and the target nozzle 122 is protected.

Incidentally, considering a time required for complete evaporation of the target material which is attached to the cooling water jacket 400 while the target material is unstable, it is preferable to move the cooling water jacket 400 upward after a predetermined time (e.g., 3 min) has elapsed since the target material is confirmed to be stabilized.

Here, in order to reduce a region of the cooling water jacket which receives heat from the plasma, it is preferable to dispose the cooling water jacket apart from the plasma as far as possible. Accordingly, the cooling water jacket is moved upward and downward in the present embodiment. Further, in the present embodiment, it is preferable to make the target passing region larger than those in the foregoing first to third embodiments, such that the target material passes through the target passing region even when the flow of the target material is unstable. In the case where the liquefied gas is used for the target material, the target nozzle is also cooled and there is almost no practical problem for the heat shield effect of the cooling water jacket (e.g., reduction of the effect).

Next, a nozzle protection device according to a fifth embodiment of the present invention will be described.

Figure 6A:
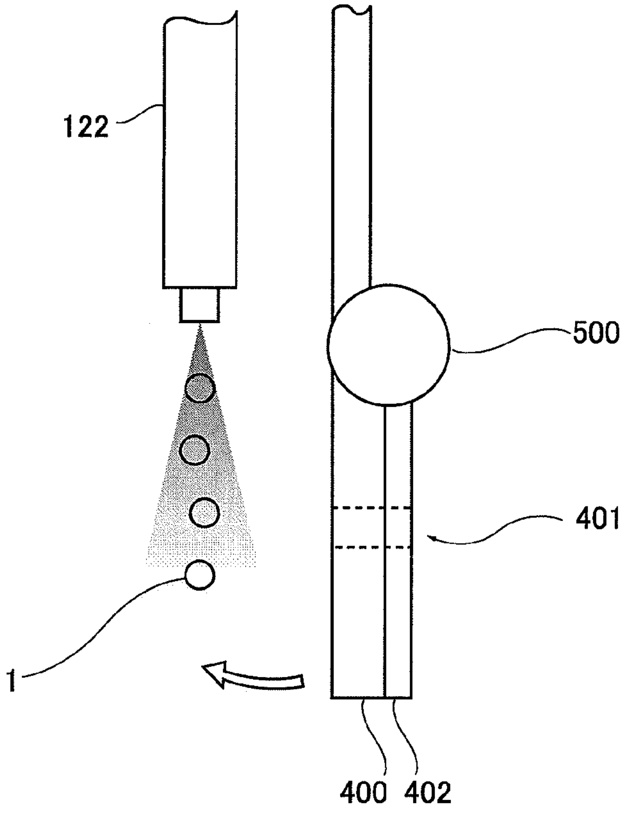
FIGS. 6A and 6B are diagrams for illustrating a nozzle protection device according to a fifth embodiment of the present invention.
Figure 6B:
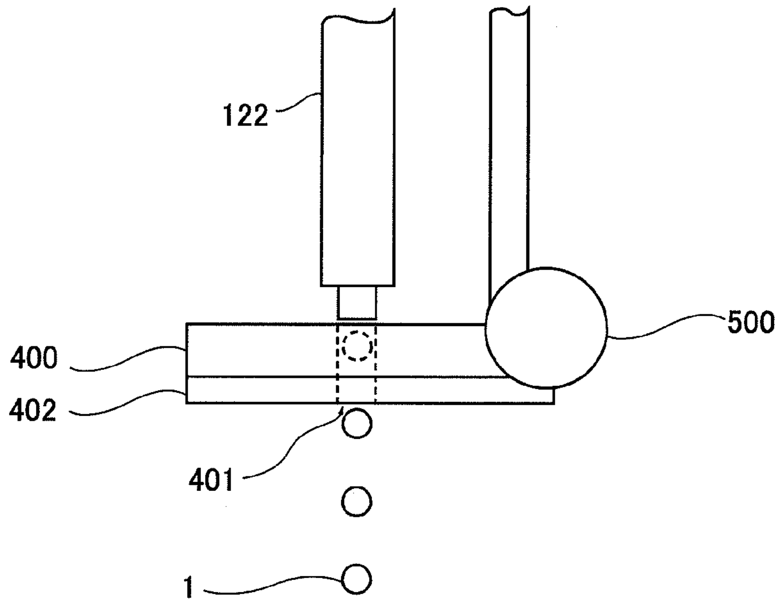

FIGS. 6A and 6B are side views showing a part of the nozzle protection device according to the fifth embodiment of the present invention. As shown in FIGS. 6A and 6B, the nozzle protection device according to the present embodiment includes an actuator 500 operating under the control of the controller 100 as shown in FIG. 1, instead of the actuator 410 shown in FIGS. 5A and 5B. Other constituents are the same as those of the forth embodiment.

The actuator 500 changes a position or an arrangement of the cooling water jacket 400 by rotating the cooling water jacket 400 around one end thereof as a center and within the vertical plane. That is, when the flow of the target material 1 is unstable, the cooling water jacket 400 is disposed along the vertical direction so as to evacuate from the flow of the target material 1 as shown in FIG. 6A. On the other hand, when the flow of the target material 1 becomes stable, the cooling water jacket 400 is rotated by 90 degrees and the target passing region 401 is disposed close to the injection outlet of the target nozzle 122 as shown in FIG. 6B. Thereby, the target material securely passes through the target passing region 401, and at the same time, the heat and the flying particles generated from the plasma is blocked to protect the target nozzle 122.

According to the present embodiment, when the flow of the target material 1 is unstable, the cooling water jacket 400 is evacuated completely from the trajectory of the target material 1, and thereby, the target material 1 is not deposited on the cooling water jacket 400. Accordingly, immediately after the flow of the target material 1 has been stabilized, the cooling water jacket 400 can be disposed under the target nozzle 122 and the generation of the EUV light can be started. That is, it is possible to reduce the tact time. Further, in the present embodiment, since the cooling water jacket 400 is disposed on the trajectory of the target material after the flow of the target material has been stabilized, the diameter of the target passing region 401 can be reduced.

Incidentally, in the present embodiment, the cooling water jacket 400 passes across the trajectory of the target material 1 when moved to the position as shown in FIG. 6B, and thereby, the target material 1 may attach onto the surface thereof. However, as described above, when the liquefied gas is used as the target material 1, the target material 1 attached to the cooling water jacket 400 is evaporated instantly and a practical problem is not caused.

Next, a nozzle protection device according to a sixth embodiment of the present invention will be described.

Figure 7A:
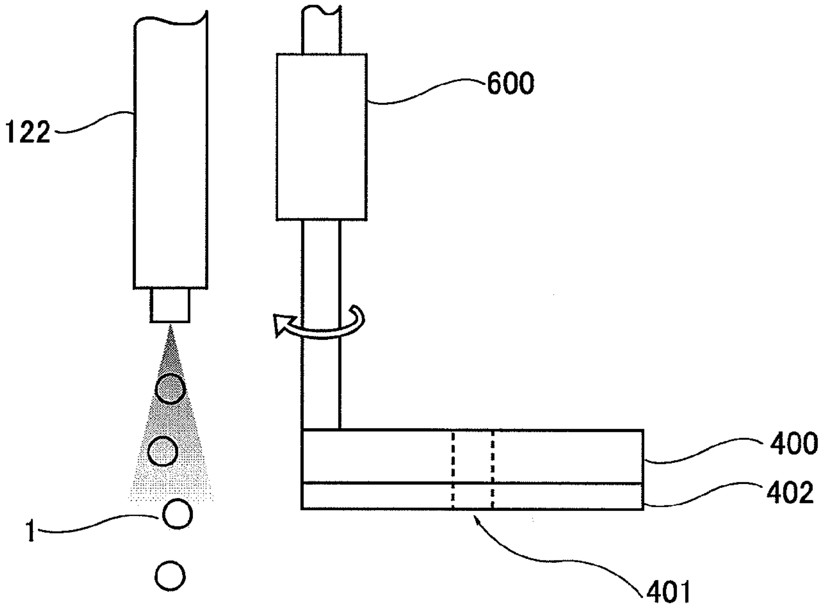
FIGS. 7A and 7B are diagrams for illustrating a nozzle protection device according to a sixth embodiment of the present invention.
Figure 7B:
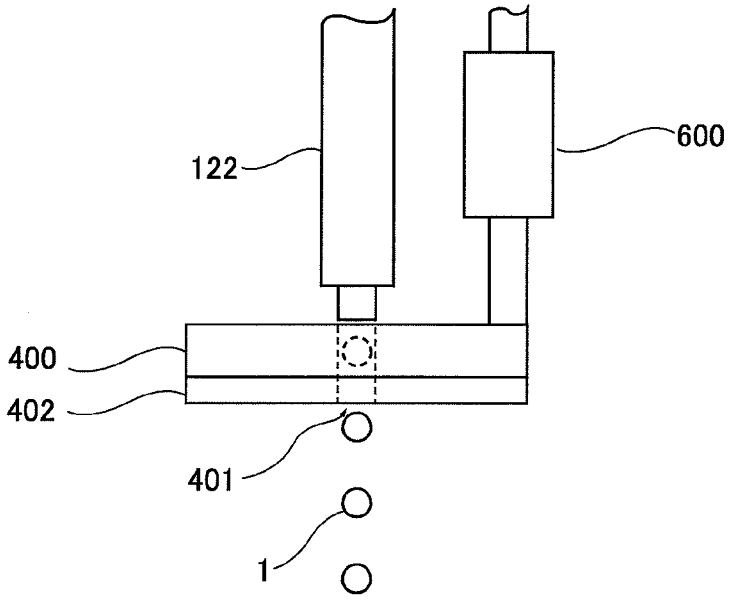

FIGS. 7A and 7B are side views showing a part of the nozzle protection device according to the sixth embodiment of the present invention. As shown in FIGS. 7A and 7B, the nozzle protection device according to the present embodiment includes an actuator 600 operating under the controller 100 as shown in FIG. 1, instead of the actuator 410 as shown in FIGS. 5A and 5B. Other constituents are the same as those of the fourth embodiment.

The actuator 600 changes a position or an arrangement of the cooling water jacket 400 by rotating the cooling water jacket 400 around one end thereof as a center and within the horizontal plane. That is, when the flow of the target material 1 is unstable, the cooling water jacket 400 is evacuated from the trajectory of the target material 1 as shown in FIG. 7A. On the other hand, when the flow of the target material 1 becomes stable, the cooling water jacket 400 is made to rotate by 180 degrees and the target passing region 401 is disposed close to the injection outlet of the target nozzle 122 as shown in FIG. 7B. Thereby, the target material 1 securely passes through the target passing region 401, and at the same time, the heat and the flying particles generated from the plasma are blocked to protect the target nozzle 122.

In the present embodiment, the cooling water jacket 400 passes across the trajectory of the target material 1 in a very short time. Further, even while the cooling water jacket 400 is being moved, the wall surface of the target passing region 401 is maintained to be approximately parallel to the trajectory of the target material 1. Thereby, the target material 1 seldom attaches to the inside of the target passing region 401. Accordingly, there is almost no fear that the ice of the liquefied gas is deposited near the injection outlet of the target nozzle 122, and it is possible to form the stable flow of the target material 1 continuously. Further, by making the rotation speed of the cooling water jacket 400 faster than the speed of the target material 1, it is possible to greatly reduce a probability that the target material 1 attaches to the cooling water jacket 400.

Resultantly, it is possible to considerably improve repeatability in the flow of the target material 1.

Incidentally, also in the present embodiment, since the cooling water jacket 400 is evacuated completely from the trajectory of the target material until the flow of the target material is stabilized, it is possible to make the diameter of the target passing region 401 small.

Next, a nozzle protection device according to a seventh embodiment of the present invention will be described.

Figure 8:
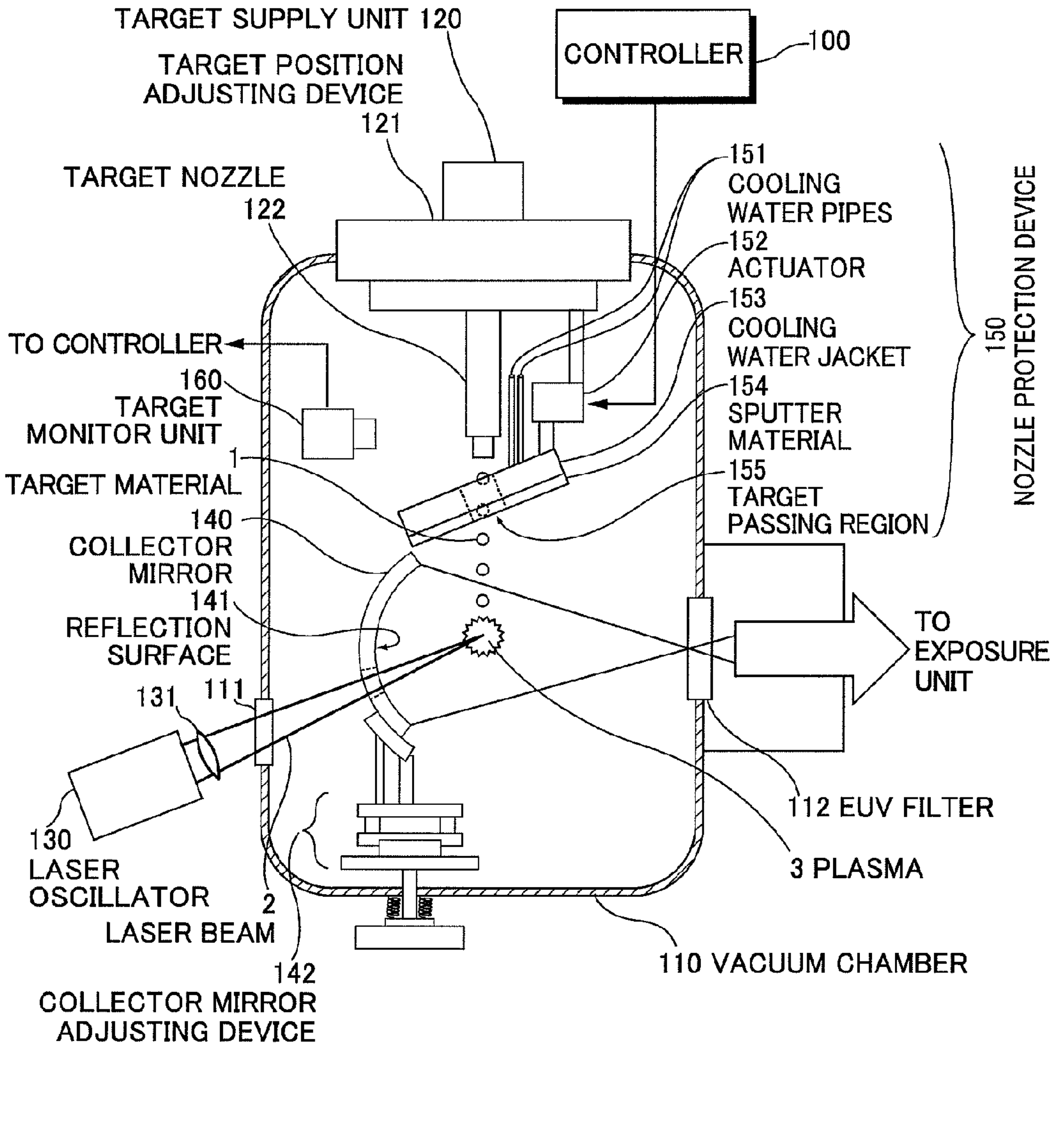
FIG. 8 is a schematic diagram showing the inside of an extreme ultraviolet light source apparatus provided with a nozzle protection device according to a seventh embodiment of the present invention.

FIG. 8 is a schematic diagram showing the inside of an EUV light source apparatus which is provided with the nozzle protection device according to the seventh embodiment of the present invention. As apparent in comparison with the nozzle protection device as shown in FIG. 1, in the present embodiment, a cooling water jacket 153 is arranged not perpendicular to the trajectory of the target material 1 but inclined by a predetermined angle from the trajectory of the target material 1. For example, the cooling water jacket 153 is arranged such that the surface disposed with the sputter material 154 faces the focusing point of the EUV light. By arranging the cooling water jacket 153 in this manner, even when the flying particles (ions or the like) from the plasma 3 hit the sputter material 154, it is possible to prevent sputtered particles generated thereby from attaching to the reflection surface 141 of the collector mirror 140. Resultantly, it is possible to extend the life of the collector mirror 140.

Incidentally, in the present embodiment, although the direction of the cooling water jacket in the nozzle protection device according to the first embodiment is changed, the cooling water jacket in each of the nozzle protection devices according to the second to fifth embodiments may be arranged in the same manner as in the present embodiment.

The operation of the nozzle protection device (specifically, operation of the actuator) is controlled by the controller 100 (FIG. 1) which controls the entire EUV light source apparatus in each of the foregoing first to seventh embodiments. However, the operation of actuator may be controlled by a controller which is separately provided for mainly controlling the operation of the nozzle protection device.

Next, a nozzle protection device according to an eighth embodiment of the present invention will be described.

Figure 9:
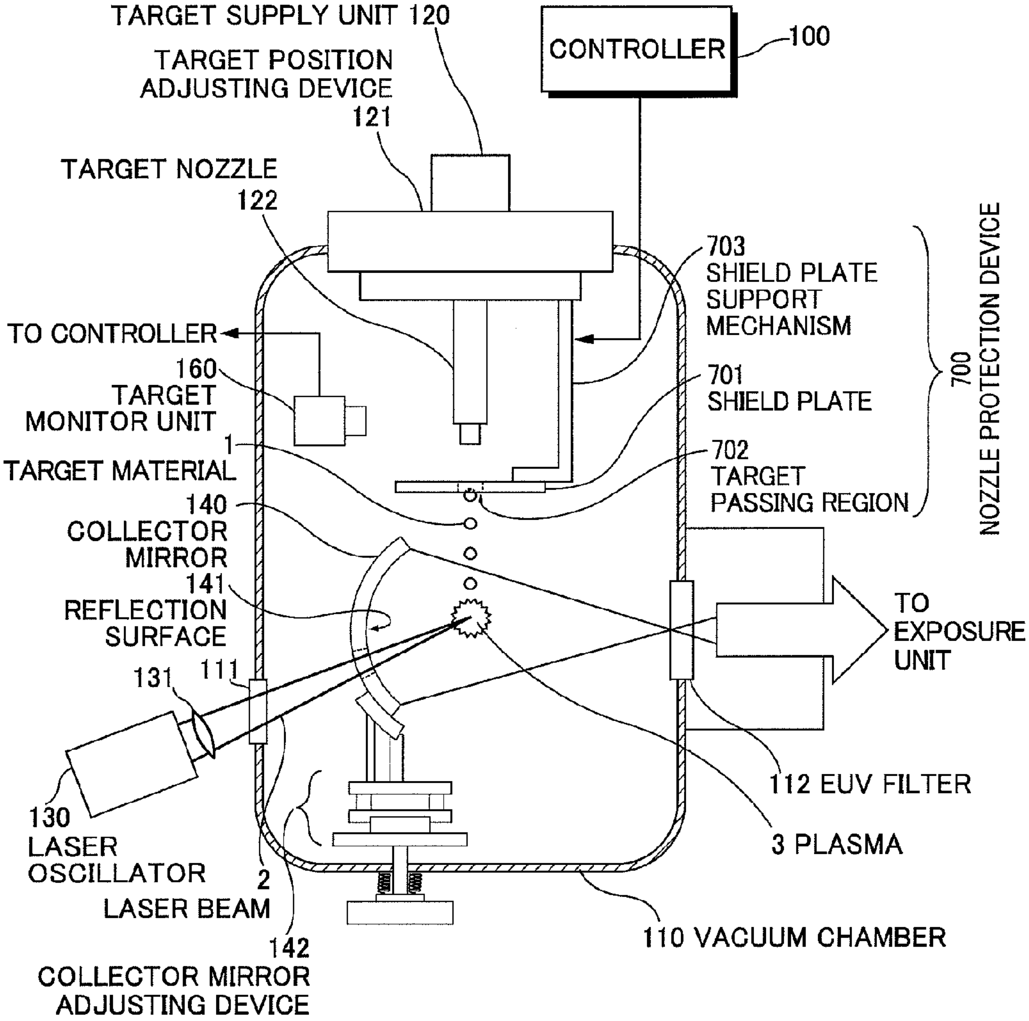
FIG. 9 is a schematic diagram showing the inside of an extreme ultraviolet light source apparatus provided with a nozzle protection device according to an eighth embodiment of the present invention.

FIG. 9 is a schematic diagram showing the inside of an EUV light source apparatus which is provided with the nozzle protection device according to the eighth embodiment of the present invention. This EUV light source apparatus includes a nozzle protection device 700 instead of the nozzle protection device 150 as shown in FIG. 1 for the first embodiment. Other points are the same as those in the first embodiment.

The nozzle protection device 700 includes a shield plate 701 formed with an opening (target passing region 702) for passing the target material 1 injected from the target nozzle 122 therethrough, and a shield plate support mechanism 703 for supporting the shield plate 701. The shield plate support mechanism 703 may move the shield plate 701 under the control of the controller 100 in the same manner as the actuators in the fourth to sixth embodiments. The nozzle protection device 700 is coupled to the target position adjusting device 121 and moved together with the target nozzle 122.

Figure 10:
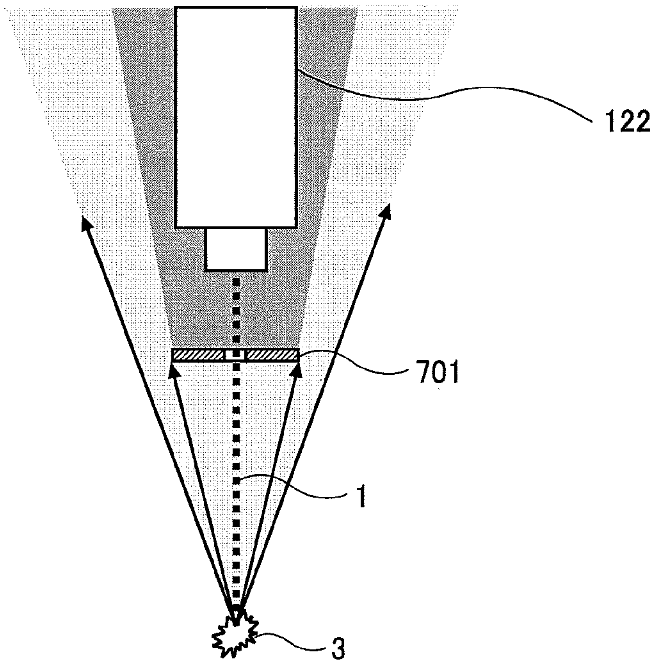
FIG. 10 is a partial cross-sectional view showing a part of a nozzle protection device according to the eighth embodiment of the present invention.

FIG. 10 is a partial cross-sectional view showing a part of the nozzle protection device according to the eighth embodiment of the present invention. As shown in FIG. 10, the shield plate 701 is provided under the target nozzle 122, and blocks the heat of the plasma 3 and the flying particles from the plasma 3, while passing the target material 1 supplied from the target nozzle 122 therethrough. The shield plate 701 may be made of stainless steel, metal resistant to the ion sputtering such as tungsten, or ceramics such as alumina or zirconia. At least the lower surface (a surface facing the plasma) of the shield plate 701 is preferably mirror-finished so as to reflect the light and the heat from the plasma 3.

Next, a nozzle protection device according to a ninth embodiment of the present invention will be described.

Figure 11:
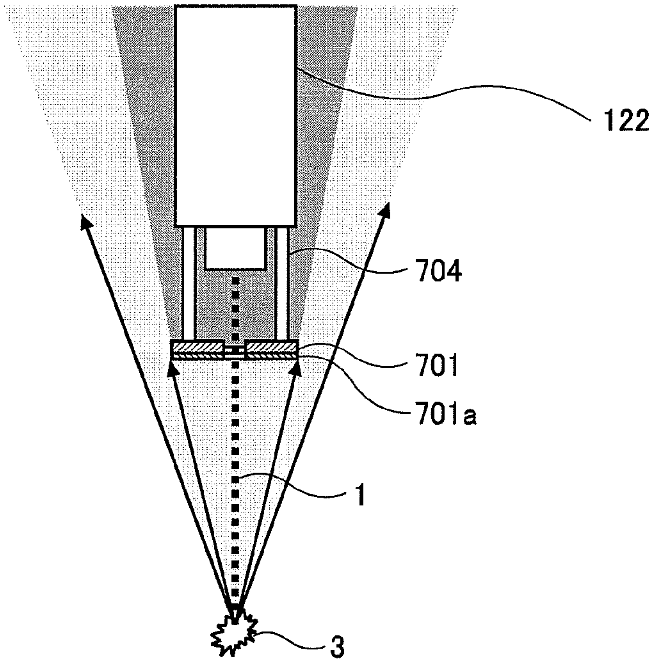
FIG. 11 is a partial cross-sectional view showing a nozzle protection device according to a ninth embodiment of the present invention.

FIG. 11 is a partial cross-sectional view showing the nozzle protection device according to the ninth embodiment of the present invention. In the present embodiment, a shield plate 701 is attached to the target nozzle 122 by using a shield plate support mechanism (support pillar 704) instead of the shield plate support mechanism 703 as shown in FIG. 9. The support pillar 704 is made of a heat insulating material such as Cerazol. According to the present embodiment, since the shield plate 701 moves following the target nozzle 122 when the position of the target nozzle 122 is adjusted, it becomes easy to pass the target material 1 supplied from the target nozzle 122 through the target passing region of the shield plate 701. Further, in the present embodiment and the other embodiments, at least the lower surface (a surface facing the plasma) of the shield plate 701 may be provided with a multilayered film 701*a* formed for reflecting light having a particular wavelength as shown in FIG. 11.

Next, a nozzle protection device according to a tenth embodiment of the present invention will be described.

Figure 12A:
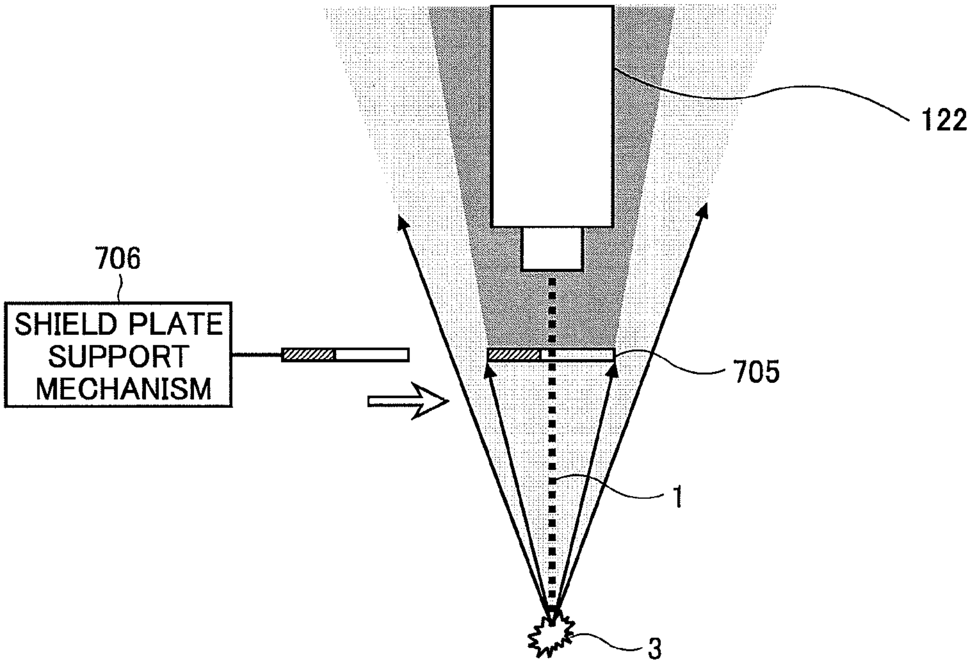
FIGS. 12A and 12B are diagrams showing a part of a nozzle protection device according to a tenth embodiment of the present invention.
Figure 12B:
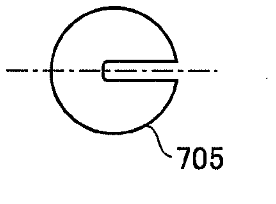

FIG. 12A is a partial cross-sectional view showing a part of the nozzle protection device according to the tenth embodiment of the present invention. FIG. 12B is a plan view showing a part of the nozzle protection device according to the tenth embodiment of the present invention. In the present embodiment, a shield plate 705 and a shield plate support mechanism 706 are used instead of the shield plate 701 and the shield plate support mechanism 703 as shown in FIG. 9. After the droplet of the target material 1 has been generated stably, the shield plate 705 is moved from the left side to the right side in the drawing by the shield plate support mechanism 706 and inserted between the target nozzle 122 and the plasma emission point (source point). So as not to disturb the travel of the droplet at this time, a long cut is formed in the shield plate 705 from the perimeter part to the center part such that the long cut reaches the target passing region. Further, when the generation of the droplet is terminated, the shield plate 705 is moved in advance from the right side to the left side in the drawing by the shield plate support mechanism 706 and removed from the position between the target nozzle 122 and the plasma emission point. According to the present embodiment, it is possible to prevent the droplet 1 from being attached to the shield plate 705, when the generation of the droplet is started or terminated.

Next, a nozzle protection device according to an eleventh embodiment of the present invention will be described.

Figure 13:
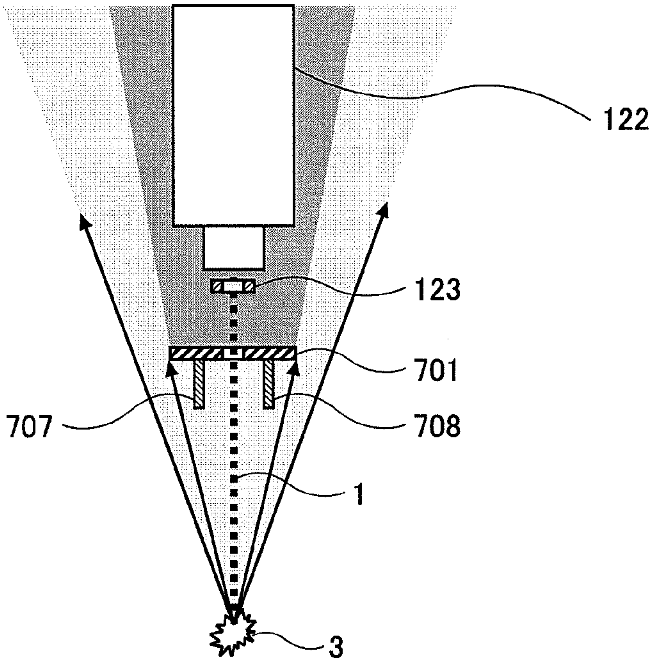
FIG. 13 is a partial cross-sectional view showing a part of a nozzle protection device according to an eleventh embodiment of the present invention.

FIG. 13 is a partial cross-sectional view showing a part of the nozzle protection device according to the eleventh embodiment of the present invention. In the present embodiment, the shield plate 701 is made of an electrical insulating material such as ceramics, and a pair of deflection electrodes 707 and 708, which generate an electric field necessary to isolate the droplet of the target material 1, are attached to the shield plate 701. Thereby, the shield plate 701 also serves as a holder of the pair of deflection electrodes 707 and 708.

In the present embodiment, the pair of deflection electrodes 707 and 708 are disposed between the shield plate 701 and the plasma emission point (source point). While a desired droplet is electrically charged in advance selectively among the consecutive droplets by using a charging electrode 123, the electrical field is generated by voltage application across the pair of deflection electrodes 707 and 708, and thereby, the trajectory of the desired droplet can be controlled so as to isolate the desired droplet. For example, when a laser beam is to be applied to one droplet among the ten consecutive droplets, one droplet is isolated among the ten consecutive droplets. Thereby, the droplets are thinned out, and it becomes possible to prevent contamination within the vacuum chamber and loss of vacuum within the vacuum chamber, which are caused by unnecessary droplet evaporation. Alternatively, while an unnecessary droplet is electrically charged in advance selectively among the contiguous droplets by using the charge electrode 123, the electric filed is generated by the voltage application across the pair of deflection electrodes 707 and 708, and thereby, the trajectory of the unnecessary droplet may be controlled so as to isolate the unnecessary droplet.

Next, a nozzle protection device according to a twelfth embodiment of the present invention will be described.

Figure 14:
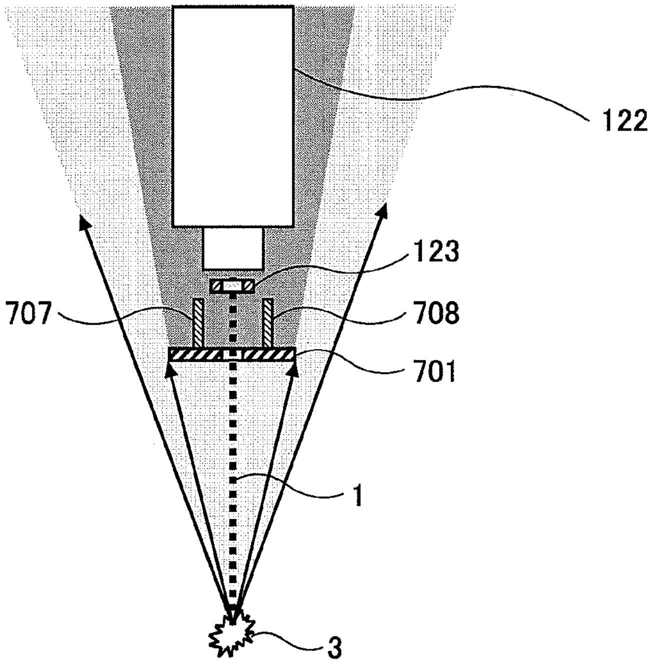
FIG. 14 is a partial cross-sectional view showing a part of a nozzle protection device according to a twelfth embodiment of the present invention.

FIG. 14 is a partial cross-sectional view showing a part of the nozzle protection device according to the twelfth embodiment of the present invention. In the present embodiment, in the same manner as in the eleventh embodiment, the shield plate 701 is made of an electrical insulating material such as ceramics, and a pair of deflection electrodes 707 and 708, which generate an electric field necessary to isolate the droplet of the target material 1, are attached to the shield plate 701. Thereby, the shield plate 701 also serves as a holder of the pair of deflection electrodes 707 and 708. In the present embodiment, the pair of deflection electrodes 707 and 708 are disposed between the target nozzle 122 and the shield plate 701.

Next, a nozzle protection device according to a thirteenth embodiment of the present invention will be described.

Figure 15:
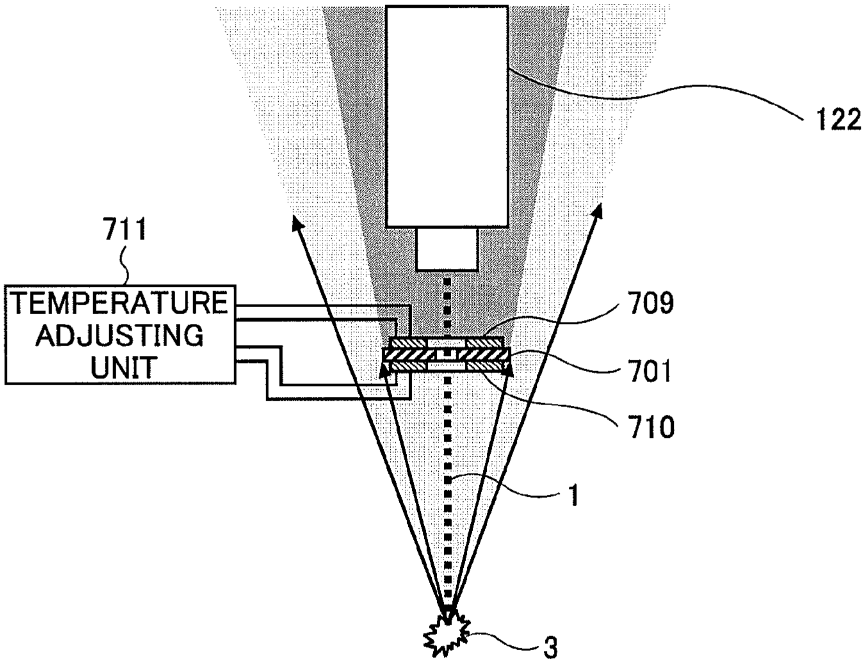
FIG. 15 is a partial cross-sectional view showing a part of a nozzle protection device according to a thirteenth embodiment of the present invention.

FIG. 15 is a partial cross-sectional view showing a part of the nozzle protection device according to the thirteenth embodiment of the present invention. In the present embodiment, a heater 709 for heating the shield plate 701 is attached to a first surface of the shield plate 701, and a temperature sensor 710 for detecting a temperature of the shield plate 701 is attached to a second surface opposite to the first surface of the shield plate 701. Further, a temperature adjusting unit 711 is provided for supplying electric power to the heater 709 according to a detection result of the temperature sensor 710. For example, in the case of employing tin (Sn) as the target material 1, the temperature adjusting unit 711 supplies electric power to the heater 709 so as to make the temperature of the shield plate 701 not less than the melting point of tin (232° C.).

Next, a nozzle protection device according to a fourteenth embodiment of the present invention will be described.

Figure 16:
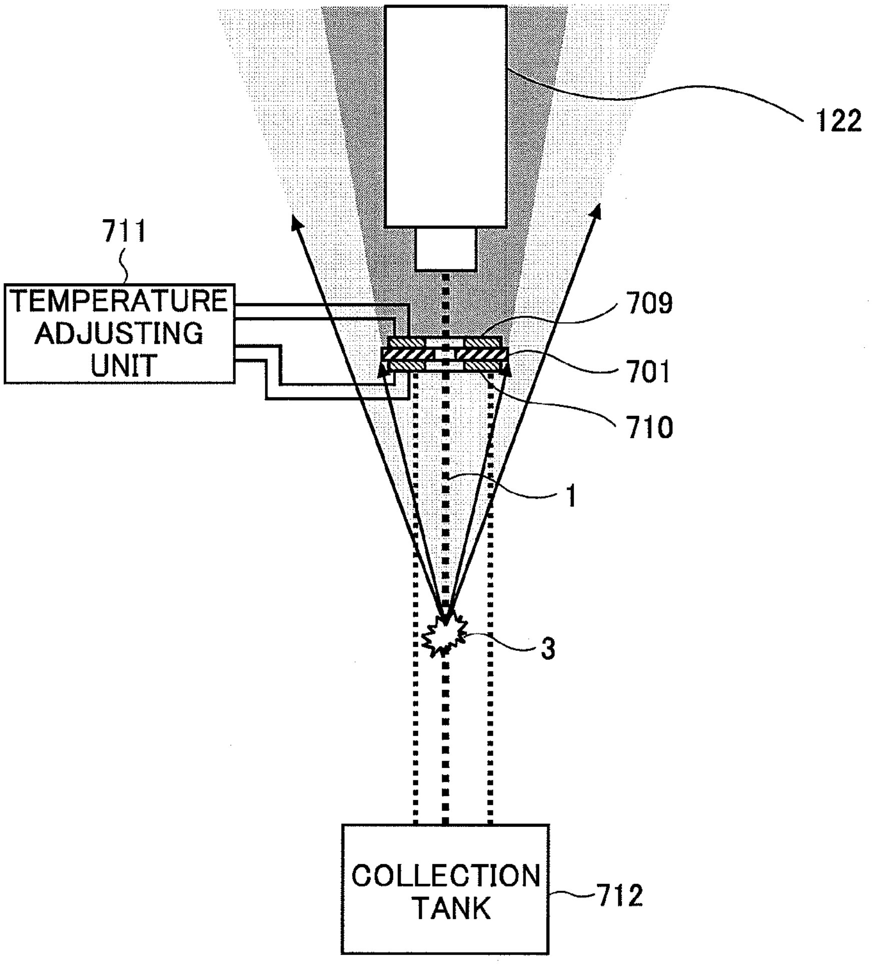
FIG. 16 is a partial cross-sectional view showing a part of a nozzle protection device according to a fourteenth embodiment of the present invention.

FIG. 16 is a partial cross-sectional view showing a part of the nozzle protection device according to the fourteenth embodiment of the present invention. In the present embodiment, a collection tank 712 is added to the thirteenth embodiment. The collection tank 712 is disposed on the opposite side of the shield plate 701 with the plasma 3 in between, and collects the target material which is heated by the heater 709 and falls in the liquid state. This collection tank 712 can also serve as a collection tank for collecting the target material which is injected from the target nozzle 122 but not irradiated with the laser beam. The collection tank 712 is provided with a collecting tower having a diameter large enough to collect the target material falling from the shield plate 701 or the temperature sensor 710. The diameter of the collecting tower is preferably larger than that of the shield plate 701.

Next, a nozzle protection device according to a fifteenth embodiment of the present invention will be described.

Figure 17:
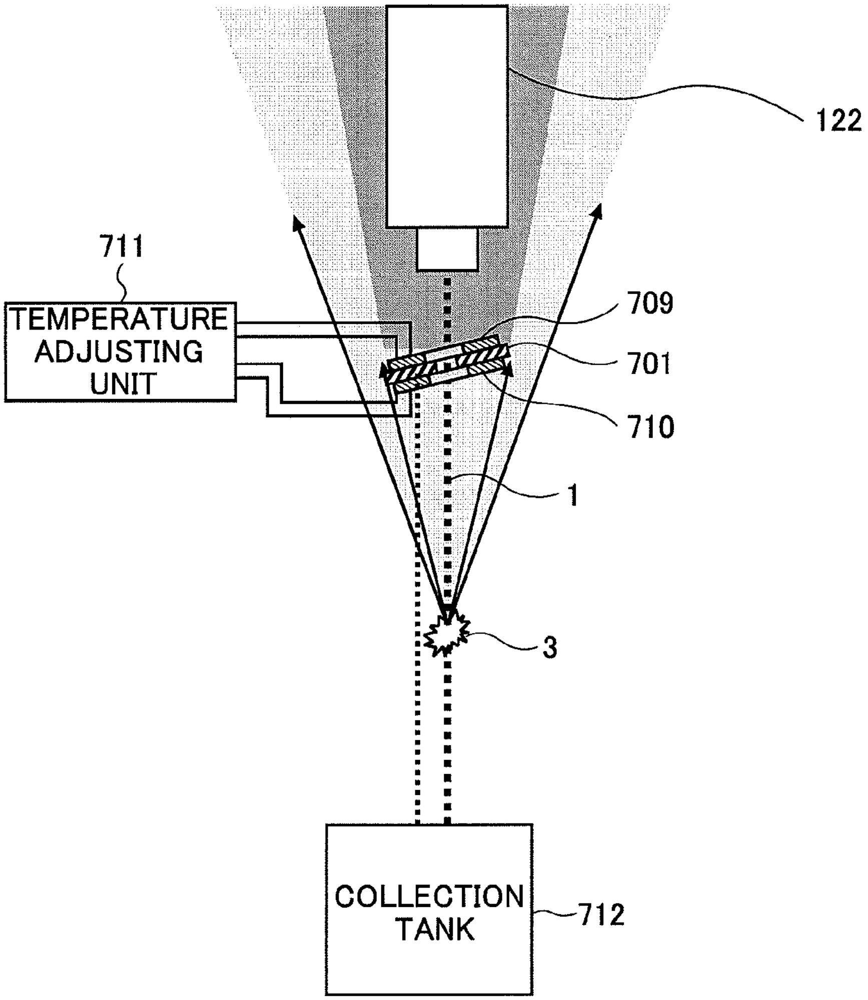
FIG. 17 is a partial cross-sectional view showing a part of a nozzle protection device according to a fifteenth embodiment of the present invention.

FIG. 17 is a partial cross-sectional view showing a part of the nozzle protection device according to the fifteenth embodiment of the present invention. In the fourteenth embodiment, the shield plate 701, the heater 709, and the temperature sensor 710 are arranged perpendicular to the vertical direction, that is, in parallel to a horizontal direction. On the other hand, in the present embodiment, the shield plate 701, the heater 709, and the temperature sensor 710 are arranged not in parallel to the horizontal direction but inclined by a predetermined angle from the horizontal direction. The target material, which is heated by the heater 709 and turned into the liquid state, flows to the lowermost ends of the shield plate 709 or the temperature sensor 710, and drops therefrom as a droplet. Accordingly, the drop points of the target material from the shield plate 701 or the temperature sensor 710 meet one another almost at one point, and thereby, the collection tank 712 may be disposed under the point and the size of the collection tank 712 can be made compact.

Next, a nozzle protection device according to a sixteenth embodiment of the present invention will be described.

Figure 18A:
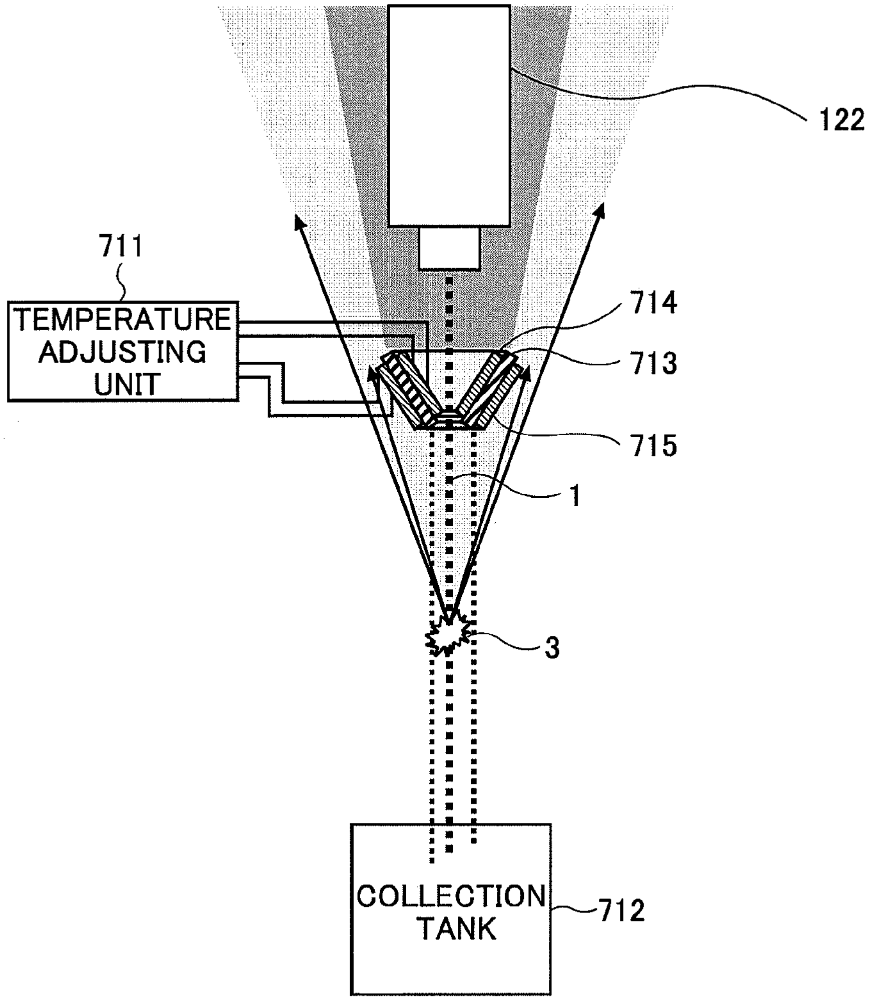
FIGS. 18A and 18B are diagrams showing a part of a nozzle protection device according to a sixteenth embodiment of the present invention.
Figure 18B:
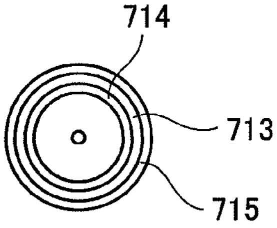

FIG. 18A is a partial cross-sectional view showing a part of the nozzle protection device according to the sixteenth embodiment of the present invention. FIG. 18B is a plan view showing a part of the nozzle protection device according to the sixteenth embodiment of the present invention. In the present embodiment, a heater 714 for heating the shield plate 713 is attached to a first surface of a shield plate 713, and a temperature sensor 715 for detecting a temperature of the shield plate 713 is attached to a second surface opposite to the first surface of the shield plate 713. Each of the shield plate 713, the heater 714, and the temperature sensor 715 has a conical shape. Further, the temperature adjusting unit 711 is provided for supplying electric power to the heater 714 according to a detection result of the temperature sensor 715. The target material 1, which is heated by the heater 714 and turned into the liquid state, flows to the center portion of the shield plate 713 or the temperature sensor 715, and drops therefrom. Accordingly, the drop points of the target material 1 in the shield plate 713 and the temperature sensor 715 meet one another almost at one point, and thereby the collection tank 712 may be disposed under the point and the size of the collection tank 712 can be made compact.

Next, a nozzle protection device according to a seventeenth embodiment of the present invention will be described.

Figure 19B:
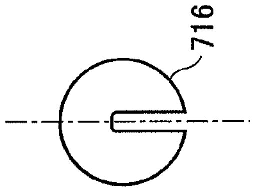
FIGS. 19A and 19B are diagrams showing a part of a nozzle protection device according to a seventeenth embodiment of the present invention.
Figure 19A:
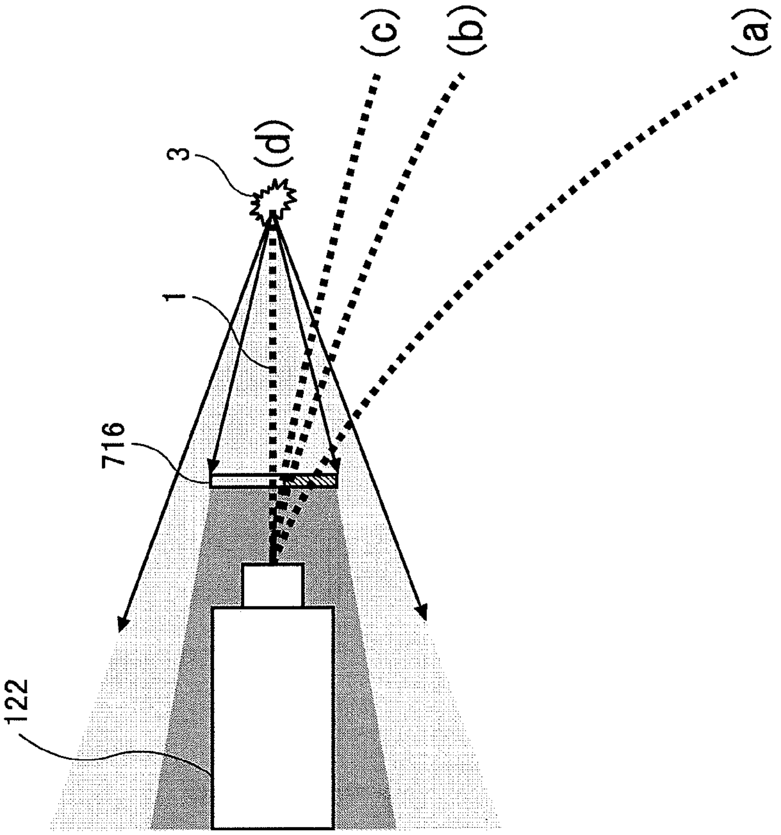

FIG. 19A is a partial cross-sectional view showing a part of the nozzle protection device according to the seventeenth embodiment of the present invention. FIG. 19B is a plan view showing a part of the nozzle protection device according to the seventeenth embodiment of the present invention. In the present embodiment, the axis of the target nozzle 122 is disposed in parallel to a horizontal direction, and the target material 1 is injected from the target nozzle 122 in the horizontal direction. Accordingly, a shield plate 716 is disposed in the vertical direction.

In the case of the horizontal injection, since the injection pressure is low in the initial injection, the droplet of the target material 1 takes trajectory (a) because of gravity. As the pressure increases, the trajectory becomes close to a horizontal trajectory gradually as trajectory (a) to trajectory (b), then to trajectory (c), and then to trajectory (d). At this time, if the shield plate 716 has a shape having the target passing region only at the center part, the target material 1 hits the shield plate 716 in the process from trajectory (a) to trajectory (c). Accordingly, in the present embodiment, a long cut is formed from the outer perimeter part (lower side in the drawing) to the center part of the shield plate 716 such that the long cut reaches the target passing region. Thereby, even for trajectories (a), (b), and (c) in the case where the injection pressure is low when the injection of the target material 1 is started or terminated, the target material 1 does not hit the shield plate 716 and smooth target supply is possible. In addition, for a nozzle protection device, it is possible to use various kinds of nozzle protection devices which have been described in the embodiments for the vertical injection (eighth to sixteenth embodiments).

The invention claimed is:

1. A target supply device to be used in an extreme ultraviolet light source apparatus for generating extreme ultraviolet light by irradiating a target material with a laser beam and thereby turning the target material into plasma, said target supply device comprising:

a nozzle configured to output the target material;

a target position adjusting mechanism configured to adjust a position of the nozzle;

a shield plate which is formed with an opening for passing the target material therethrough; and a shield plate support mechanism which is coupled to the target position adjusting mechanism and configured to support said shield plate.

2. The target supply device according to claim 1, wherein at least a surface of said shield plate facing the plasma is mirror-finished.

3. The target supply device according to claim 1, wherein a multilayered film configured to reflect light having a particular wavelength is formed at least on a surface of said shield plate facing the plasma.

4. The target supply device according to claim 1, wherein said shield plate support mechanism includes a heat insulating pillar configured to support said shield plate at a predetermined position against said nozzle.

5. The target supply device according to claim 1, further comprising:

a charging electrode configured to electrically charge the target material; and a pair of deflection electrodes configured to control a trajectory of the charged target material.

6. The target supply device according to claim 1, wherein the opening of the shield plate is a cut formed from a perimeter part to a center part of the shield plate, said cut passing the target material therethrough.

7. The target supply device according to claim 1, wherein said shield plate support mechanism is configured to insert said shield plate between said nozzle and a plasma emission point after a droplet of the target material is generated.

8. An extreme ultraviolet light source apparatus for generating extreme ultraviolet light by irradiating a target material with a laser beam supplied from an outside and thereby turning the target material into plasma, said extreme ultraviolet light source apparatus comprising:

a chamber in which the extreme ultraviolet light is generated;

optics configured to reflect and focus a predetermined wavelength component of light radiated from the target material turned into the plasma; and a target supply device including a nozzle configured to supply the target material into the chamber, a target position adjusting mechanism configured to adjust a position of the nozzle, a shield plate which is formed with an opening for passing the target material therethrough, and a shield plate support mechanism which is coupled to the target position adjusting mechanism and configured to support said shield plate.

9. A target supply device to be used in an extreme ultraviolet light source apparatus for generating extreme ultraviolet light by irradiating a target material with a laser beam and thereby turning the target material into plasma, said target supply device comprising:

a nozzle configured to output the target material;

a target position adjusting mechanism configured to adjust a position of the nozzle;

a shield plate which is formed with an opening for passing the target material therethrough;

a shield plate support mechanism which is coupled to the target position adjusting mechanism and configured to support said shield plate;

a heater which is attached to said shield plate and configured to heat said shield plate;

a temperature sensor which is attached to said shield plate and configured to detect a temperature of said shield plate; and a temperature adjusting unit configured to supply electric power to said heater according to a detection result of said temperature sensor.

10. The target supply device according to claim 9, further comprising:

a collection tank configured to collect the target material which is heated by said heater to fall in a liquid state.

11. The target supply device according to claim 9, wherein said shield plate, said heater, and said temperature sensor are arranged to be inclined by a predetermined angle from a horizontal direction.

12. The target supply device according to claim 9, wherein each of said shield plate, said heater, and said temperature sensor has a conical shape.

13. An extreme ultraviolet light source apparatus for generating extreme ultraviolet light by irradiating a target material with a laser beam supplied from an outside and thereby turning the target material into plasma, said extreme ultraviolet light source apparatus comprising:

a chamber in which the extreme ultraviolet light is generated;

optics configured to reflect and focus a predetermined wavelength component of light radiated from the target material turned into the plasma; and a target supply device including a nozzle configured to supply the target material into the chamber, a target position adjusting mechanism configured to adjust a position of the nozzle, a shield plate which is formed with an opening for passing the target material therethrough, a shield plate support mechanism which is coupled to the target position adjusting mechanism and configured to support said shield plate, a heater which is attached to said shield plate and configured to heat said shield plate, a temperature sensor which is attached to said shield plate and configured to detect a temperature of said shield plate, and a temperature adjusting unit configured to supply electric power to said heater according to a detection result of said temperature sensor.

14. The target supply device according to claim 1, further comprising a vibration mechanism configured to vibrate the nozzle.

15. The extreme ultraviolet light source apparatus according to claim 8, wherein the target supply device further includes a vibration mechanism configured to vibrate the nozzle.

16. The extreme ultraviolet light source apparatus according to claim 8, wherein the target supply device further includes:

a charging electrode configured to electrically charge the target material; and a pair of deflection electrodes configured to control a trajectory of the charged target material.

17. The target supply device according to claim 9, wherein the temperature adjusting unit is configured to supply electric power to said heater according to a detection result of said temperature sensor to make the temperature of the shield plate not less than a melting point of the target material.

18. The target supply device according to claim 9, further comprising a vibration mechanism configured to vibrate the nozzle.

19. The target supply device according to claim 9, further comprising:

a charging electrode configured to electrically charge the target material; and a pair of deflection electrodes configured to control a trajectory of the charged target material.

20. The extreme ultraviolet light source apparatus according to claim 13, wherein the temperature adjusting unit is configured to supply electric power to said heater according to a detection result of said temperature sensor to make the temperature of the shield plate not less than a melting point of the target material.

21. The extreme ultraviolet light source apparatus according to claim 13, wherein the target supply device further includes a vibration mechanism configured to vibrate the nozzle.

22. The extreme ultraviolet light source apparatus according to claim 13, wherein the target supply device further includes:

a charging electrode configured to electrically charge the target material; and a pair of deflection electrodes configured to control a trajectory of the charged target material.

* * * * *